United States Patent
Wang et al.

(10) Patent No.: US 9,987,207 B1
(45) Date of Patent: Jun. 5, 2018

(54) FOAMING WARMING CLEANSER

(71) Applicant: L'OREAL, Paris (FR)

(72) Inventors: Camillia Wang, Edison, NJ (US); Carol Ragai Elmasry, South Amboy, NJ (US); Mickael Poletti, Shanghai (CN)

(*) Notice: Subject to any disclaimer, the term of this patent is extended or adjusted under 35 U.S.C. 154(b) by 0 days. days.

(21) Appl. No.: 15/637,553

(22) Filed: Jun. 29, 2017

(51) Int. Cl.
| | |
|---|---|
| *A61K 6/05* | (2006.01) |
| *A61K 8/34* | (2006.01) |
| *A61K 8/44* | (2006.01) |
| *A61K 8/46* | (2006.01) |
| *A61Q 19/10* | (2006.01) |

(52) U.S. Cl.
CPC .............. *A61K 8/345* (2013.01); *A61K 8/442* (2013.01); *A61K 8/463* (2013.01); *A61Q 19/10* (2013.01); *A61K 2800/242* (2013.01); *A61K 2800/28* (2013.01); *A61K 2800/31* (2013.01); *A61K 2800/48* (2013.01)

(58) Field of Classification Search
None
See application file for complete search history.

(56) References Cited

U.S. PATENT DOCUMENTS

| | | | |
|---|---|---|---|
| 6,162,775 | A | 12/2000 | Methmanus-Spaltro |
| 6,287,580 | B1 | 9/2001 | Gott et al. |
| 6,309,622 | B1 | 10/2001 | Minnix |
| 7,214,381 | B2 | 5/2007 | Shefer et al. |
| 7,700,530 | B2 | 4/2010 | Mundschau et al. |
| 2006/0067957 | A1 | 3/2006 | Hwang et al. |
| 2010/0111887 | A1 | 5/2010 | Senee et al. |

FOREIGN PATENT DOCUMENTS

EP 0027730 A2 4/1981

*Primary Examiner* — Necholus Ogden, Jr.

(57) ABSTRACT

The present disclosure relates to anhydrous foaming cleanser compositions, which generally include: a) one or more foaming surfactants selected from the group consisting of sodium lauroyl glutamate and diethylhexyl sodium sulfosuccinate, wherein the total amount of foaming surfactant is at least about 8% by weight of the total weight composition; b) a first and a second polyol; c) from about 28% to about 50% by weight of a third polyol selected from the group consisted of PEG-4, PEG-6, PEG-8, and mixture thereof; d) a thickener agent selected from the group consisting of polyacrylate crosspolymer-1, polyacrylate crosspolymer-6, polyacrylate crosspolymer-9, polyacrylate crosspolymer-11, and the mixtures thereof.

24 Claims, 3 Drawing Sheets

FOAMING WARMING CLEANSER

FIELD OF THE DISCLOSURE

The present disclosure specifically relates to an anhydrous foaming warming cleanser composition.

BACKGROUND

Today's market includes many existing products and formulations that achieve cleaning of the skin by removing or exfoliating the upper layers of the epidermis, which typically contains dead skin cells. A variety of approaches have been developed to obtain better cleaning efficacy from cosmetic products.

Consumers in the deep cleansing segment look for cleansers that can gently cleanse the pore and improve the texture and tone of the skin. Warming cleansers can help in opening up pores, gently exfoliate skin. They can also be used in combination with a brush head device.

One major technology for the warming cleansers on the market is the use of inorganic salts or zeolites which break down when in contact with water, producing an exothermic reaction. Foaming is also particularly important for most consumers as the bubbles and leathering signify the deep cleanse. Formulating a warming and foaming cleanser with a glycol base that can work synergistically with or without a device will be the response to the consumer needs to fill this gap.

SUMMARY OF THE DISCLOSURE

The warming foaming cleansing compositions of the instant disclosure provide unexpected levels of temperature increase. The cleansing compositions are particularly unique in that they are foaming, thus providing a nice warming feel during use, and are surprisingly effective at removing makeup from the skin. Finally, the cleansing compositions are very stable, which is important for providing a long-lasting and durable product for consumers.

The anhydrous warming foaming cleanser compositions of the instant disclosure typically include the following:
  a) one or more foaming surfactants selected from the group consisting of sodium lauroyl glutamate and diethylhexyl sodium sulfosuccinate,
  wherein the total amount of foaming surfactant is at least about 8% by weight of the total weight of the composition;
  b) a first and a second polyol;
  c) from about 28% to about 50% by weight of a third polyol selected from the group consisting of PEG-4, PEG-6, PEG-8, and the mixtures thereof;
  d) a thickener agent selected from the group consisting of polyacrylate crosspolymer-1, polyacrylate crosspolymer-6, polyacrylate crosspolymer-9, polyacrylate crosspolymer-11, and the mixtures thereof.

In one or more embodiments, the composition produces a warming effect when mixed with water during a cleansing process. In some embodiments, the one or more foaming surfactants are present in an amount from about 8% to about 15% by weight of the total weight of the composition. In some embodiments, the one or more foaming surfactants are present in an amount from about 8% to about 10% by weight of the total weight of the composition.

In one or more embodiments, the first polyol is propylene glycol. In some embodiments, the second polyol is glycerin. In some embodiments, the first polyol is present in an amount from about 20% to about 40% by weight of the total weight of the composition. In or more embodiments, the first polyol is present in an amount from about 23% to about 33% by weight of the total weight of the composition. In some embodiments, the first polyol is present in an amount from about 25% to about 28% by weight of the total weight of the composition. In some embodiments, the second polyol is present in an amount from about 10% to about 60% by weight of the total weight of the composition. In one or more embodiments, the second polyol is present in an amount from about 15% to about 50% by weight of the total weight of the composition. In some embodiments, the second polyol is present in an amount from about 18% to about 40% by weight of the total weight of the composition.

In some embodiments, the third polyol comprises PEG-8. In some embodiments, PEG-8 is present in an amount from about 25% to about 50% by weight of the total weight of the composition. In some embodiments, PEG-8 is present in an amount from about 25% to about 50% by weight of the total weight of the composition. In some embodiments, PEG-8 is present in an amount from about 30% to about 45% by weight of the total weight of the composition. In other embodiments, PEG-8 is present in an amount from about 35% to about 40% by weight of the total weight of the composition.

In one or more embodiments, the thickener agent comprises polyacrylate crosspolymer-6. In some embodiments, the thickener agent is present in an amount from about 0.1% to about 2% by weight of the total weight of the composition. In some embodiments, the thickener agent is present in an amount from about 0.5% to about 1.5% by weight of the total weight of the composition. In some other embodiments, the thickener agent is present in an amount from about 0.7% to about 1.2% by weight of the total weight of the composition.

In one or more embodiments, the compositions can further comprise a warming enhancer selected from the group consisting of tocopheryl nicotinate, vanillyl butyl ether, ginger, *capsicum* extract, volcanic ash.

In one or more embodiments, the warming enhancer comprises tocopheryl nicotinate.

Another aspect of the instant disclosure can include the following:
  a) sodium lauroyl glutamate and diethylhexyl sodium sulfosuccinate;
  b) propylene glycol and glycerin;
  c) a polyacrylate crosspolymer-6;
  d) PEG-8; and
  e) tocopherol nicotinate.

Another aspect of the present disclosure can include a method of cleansing skin. In some embodiments, the method comprises applying to skin a mixture of water and the composition of claim 1; and applying a manual or sonic energy to the mixture to cleanse the skin.

BRIEF DESCRIPTION OF THE DRAWINGS

Implementations of the present technology will now be described, by way of example only, with reference to the attached figures, wherein.

Figure 1:
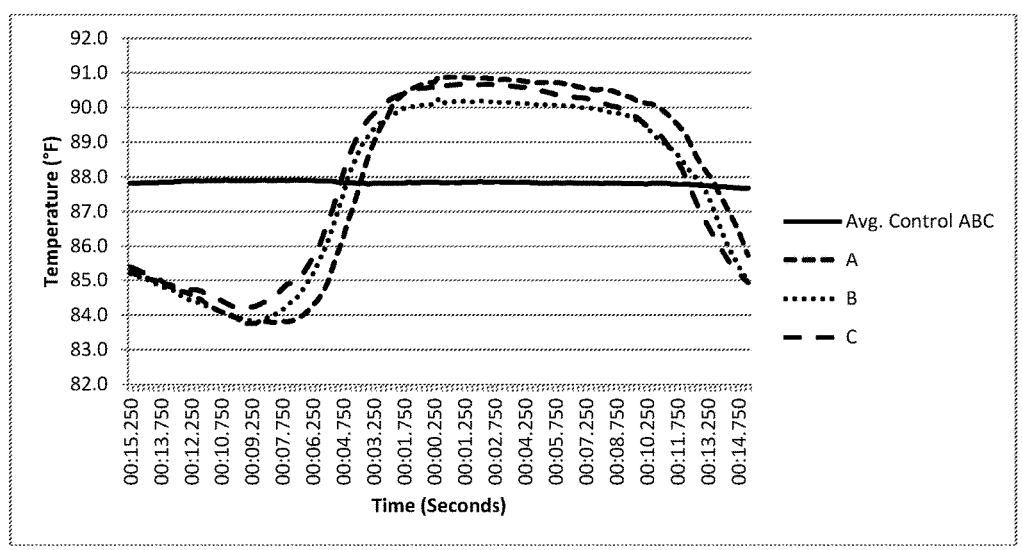
FIG. 1 graphically represents the skin surface temperature over time and compares the temperature increase as a function of time for three exemplary compositions when the skin is subjected to manual application.
Figure 2:
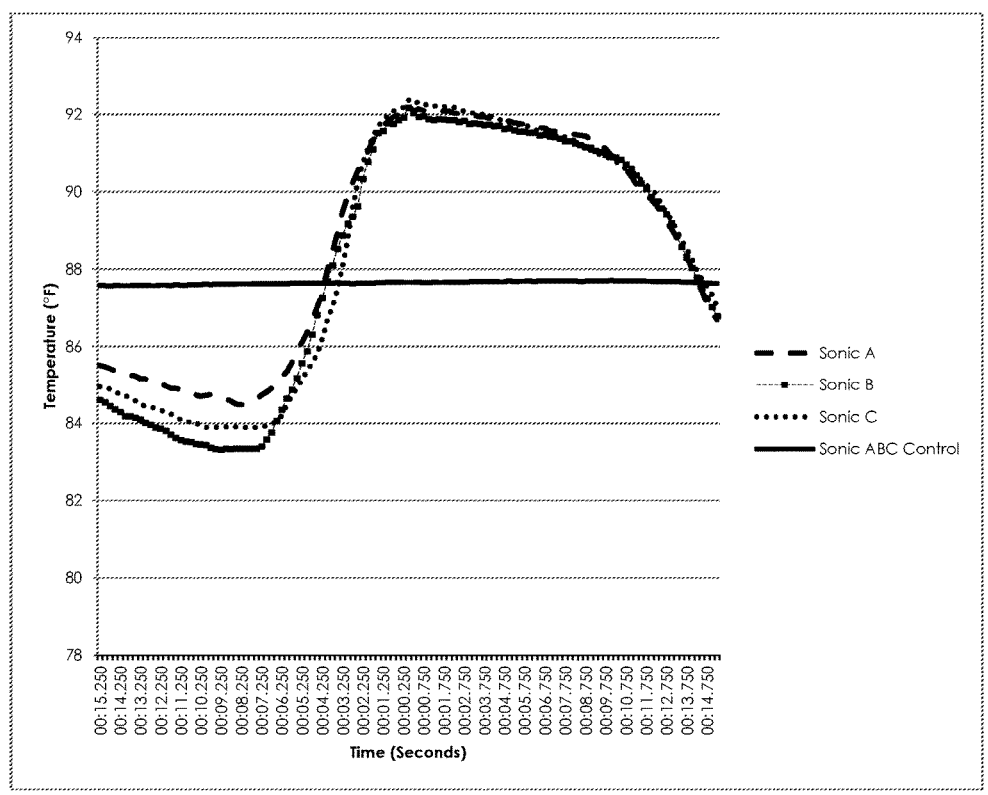
FIG. 2 graphically compares the temperature increase as a function of time for three exemplary compositions of the present disclosure subjected to sonic cleansing. A control is also represented.

It should be understood that the various aspects are not limited to the arrangements and instrumentality shown in the drawings.

DETAILED DESCRIPTION OF THE DISCLOSURE

The anhydrous warming foaming cleanser compositions of the instant disclosure, in their broadest sense, typically include the following:
a) one or more foaming surfactants selected from the group consisting of sodium lauroyl glutamate and diethylhexyl sodium sulfosuccinate, wherein the total amount of foaming surfactant is at least about 8% by weight of the total weight of the composition;
b) a first and a second polyol;
c) from about 28% to about 50% by weight of a third polyol selected from the group consisting of PEG-4, PEG-6, PEG-8, and the mixtures thereof;
d) a thickener agent selected from the group consisting of polyacrylate crosspolymer-1, polyacrylate crosspolymer-6, polyacrylate crosspolymer-9, polyacrylate crosspolymer-11, and the mixtures thereof.

Without being bound by theory, it is believed that the polyols participate in the exothermic action. Additionally, without wishing to be bound by theory, it is believed that better cleansing can be achieved at higher temperatures, for example, as pores open and as make-up is more prone to dissolving.

Foaming Surfactants

In some embodiments, the at least one foaming surfactant of (a) can be, for example, a compound selected from the group consisting of sodium lauroyl glutamate, sodium lauryl sulfate, disodium lauryl sulfosuccinate, diethylhexyl sodium sulfosuccinate, sodium cocoyl glycinate, potassium cocoyl glycinate, and the mixtures thereof.

The first foaming surfactant may be present from about 5%, 5.5%, 6%, 6.5%, 8%, 10%, 12% or 15% to about 7.5%, 8%, 8.5%, 9%, 9.5%, 10%, 11%, 12% or 15% by weight of the total weight of the composition. In some embodiments, the first foaming surfactant is sodium lauroyl glutamate.

In some embodiments, the second foaming surfactant may be present in an amount from about 0.1%, 0.5%, 1%, 1.5%, 2%, 2.5%, 3%, 4%, 5%, 6% to about 6%, 8%, 10%, 12%, 15%, 18%, 20% by weight of the total weight of the composition. In one or more embodiments, the second foaming surfactant is diethylhexyl sodium sulfosuccinate.

Surfactants in the composition include a single surfactant or a mixture of surfactants (often surfactant powders or in other easily used forms (liquid)). In one embodiment, the composition includes at least one ionic surfactant that includes anionic or amphoteric surfactants.

Examples of anionic surfactants include surfactants selected from these classes of surfactants: alkyl sulfates, alkyl ether sulfates, alkyl monoglyceride sulfates, alkyl monoglyceride sulfonates, alkylaryl sulfates, alkyl sulfosuccinates, alkyl ether sulfosuccinates, alkyl sulfosuccinamates, alkyl ether carboxylates, alkyla idoether carboxylates, alkyl succinates, fatty acyl taurates, fatty acyl isethionates, fatty acyl sarcosinates, fatty acyl glutamates, and alkyl phosphates. Alternative surfactants may include or be combined with foaming surfactants or foaming agents suitable for use in foaming skin cleansers or on skin cleaning fibrous pads when mixed with water. The foaming action provided surfactant use aids in exfoliation of skin cells and additional cleaning benefits allowing a crisp clean feel following wash-off by a user.

In selected embodiments, the surfactants are those which can be used in an anhydrous system, such as sodium lauroyl glutamate and diethylhexyl sodium sulfosuccinate. In other selected embodiments, the surfactants are those of sulfosuccinates, sulfosuccinamates, and glycinate, and the mixtures thereof.

Examples of amphoteric surfactants include surfactants selected from these classes of surfactants: amphocarboxylates, alkyl betaines, amidoalkyl betaines, amphophosphates, phosphobetaines, pyrophosphobetaines, carboxyalkyl polyamines, and amidoalkyl sultaines. In selected embodiments, the preferred surfactants are those having C10 to C16 in their fatty acyl part.

In alternative embodiments, the surfactant may include suitable nonionic surfactants including alkyl polyglucoside having alkyl groups from C10 to C16, and optionally cocoamidopropyl amine oxide.

Polyols

In addition to the components described above, the anhydrous foaming cleansing compositions can additionally include (b) polyols. Non-limiting examples of polyols, in addition to propylene glycol, are dipropylene glycol, butylene glycol, hexylene glycol, polyethylene glycol, and polyethylene glycols having a molecular weight of less than 600, such as PEG-8 (or polyethylene 400), the sugars such as sorbitol, and the mixtures thereof.

The propylene glycol and/or other alkylene glycols may be present in an amount from about 20%, 21%, 22% or 25% to about 25%, 28%, 30%, 35%, 36%, 37%, 38%, 39% or 40% by weight based on the total weight of the composition. In some embodiments, the alkylene glycol is propylene glycol.

The glycerin and/or other alkylene glycols may be present in an amount from about 10%, 11%, 12%, 14%, 16%, 18%, 20%, 25% or 30% to about 30%, 32%, 34%, 36%, 38%, 40%, 45%, 50%, 55% or 60% by weight based on the total weight of the composition. In some embodiments, the alkylene glycol is glycerin.

The cleansing compositions described herein may include one or more polyols. The polyols are chosen in an appropriate manner according to the heating effect they produced.

The quantity of polyol(s) depends on the heating effect desired. In one embodiment, the polyol is present from about 20% to about 40% by weight of the total weight of the composition. In one embodiment, the polyol is present from about 25% to about 35% by weight of the total weight of the composition. In one embodiment, the polyol is present from about 28% to about 30% by weight of the total weight of the composition.

In one embodiment, the glycerin is present from about 10% to about 60% by weight of the total weight of the composition. In one embodiment, the polyol is present from about 15% to about 40% by weight of the total weight of the composition. In one embodiment, the polyol is present from about 20% to about 30% by weight of the total weight of the composition.

As polyols, there may be mentioned in particular the polyols having at least 2 hydroxyl groups and at least 3 carbon atoms, such as glycerine, diglycerine, and the glycols such as propylene glycol, dipropylene glycol, butylene glycol, hexylene glycol, polyethylene glycol, and polyethylene glycols having a molecular weight of less than 600, such as PEG-4, PEG-6, PEG-8 (or polyethylene 400), the sugars such as sorbitol, and the mixtures thereof.

As polyols, glycerine, butylene glycol, propylene glycol, dipropylene glycol, PEG-8 and the mixtures thereof are used in one or more embodiments.

The polyethylene glycols may be present in an amount from 28%, 29%, 30%, 35% to about 35%, 36%, 37%, 38%, 40%, 45% and 50% by weight based on the total weight of the composition.

Polymer

As mentioned above, the cleansing compositions typically include (d) a thickener agent selected from the group consisting of polyacrylate crosspolymer-1, polyacrylate crosspolymer-6, polyacrylate crosspolymer-9, polyacrylate crosspolymer-11, and the mixtures thereof.

The crosslinked polyacrylate polymers may be present in an amount from about 0.1% to about 2% by weight based on the total weight of the composition.

Non-limiting examples of various types of thickeners include crosslinked polyacrylate polymers useful as thickeners or gelling agents including both cationic and nonionic polymers. Examples of useful crosslinked nonionic polyacrylate polymers and crosslinked cationic polyacrylate polymers are those described in U.S. Pat. No. 5,100,660, U.S. Pat. No. 4,849,484, U.S. Pat. No. 4,835,206, U.S. Pat. No. 4,628,078 U.S. Pat. No. 4,599,379 and EP 228,868, which are all incorporated herein by reference in their entirety.

Anhydrous Composition

The purpose of the anhydrous medium is to support the exothermic heating agent without activating it prior to exposure to water.

As used herein, the term "anhydrous" refers to a composition that contains 5% or less of water, by weight, based on total weight of the composition. In one embodiment, the composition has 3% or less of water. In one embodiment, the composition has 1% or less of water.

As used herein, the term "anhydrous" means that no water is added to the composition and water is contained only in the form of the constitutional water which in some cases cannot be avoided and is brought in as part of the ingredients in very small amounts.

Warming Enhancers

The cleansing compositions can also include more warming enhancers or derivative thereof. For example, the warming enhancer can be a compound selected from the group consisting of tocopheryl nicotinate, vanillyl butyl ether, ginger, *capsicum* extract, volcanic ash.

In some embodiments, the warming enhancer may be present in an amount from about 0.01%, 0.05%, 1%, or 1.1%, to about 1.1%, 1.5%, 2%, 2.5%, 3% by weight of the total weight of the composition. In one or more embodiments, the warming enhancer is tocopheryl nicotinate.

Figure 3:
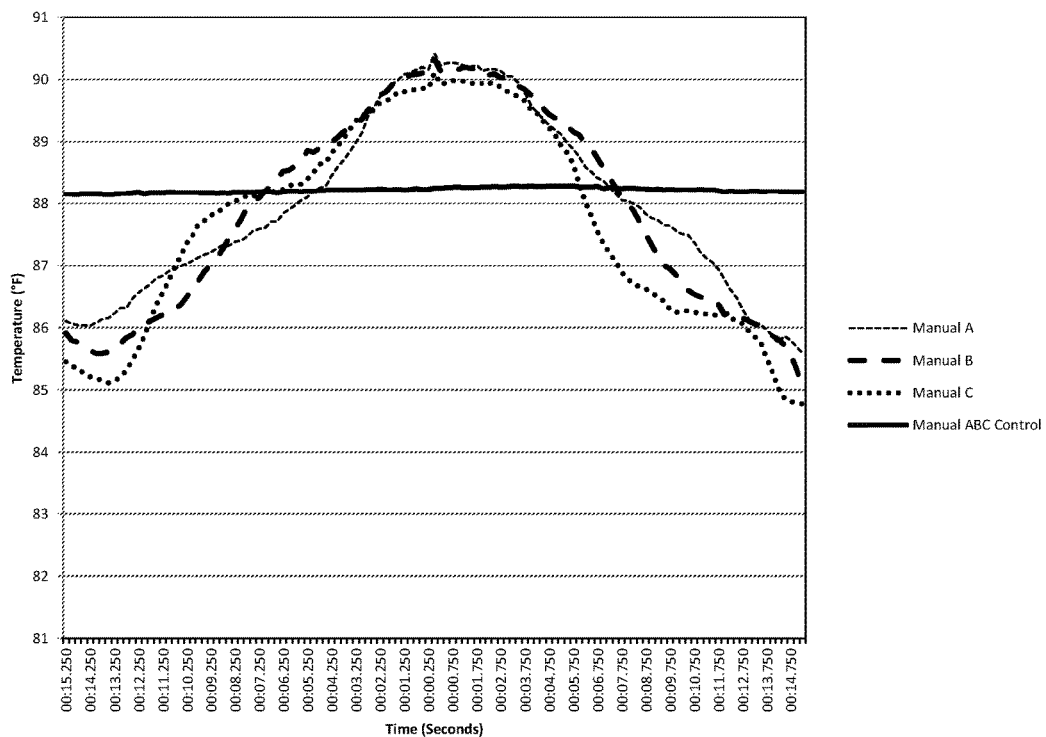
FIG. 3 graphically compares the temperature increase as a function of time for three exemplary compositions of the present disclosure subjected to manual cleansing. A control is also represented.

In one embodiment, the composition is configured to provide a minimum temperature increase by warming at least 3° C. upon exposure to water and mixing energy. For example, in one comparison, activating an exemplary composition according to FIG. 3 by hand yielded a temperature rise of about 2-3° C. Using a Clarisonic® brush, the same composition generates a rise in temperature of about 2-4° C.

In one embodiment, the composition is configured to warm for at least 12 seconds upon exposure to water and manual mixing energy and for at least 17 seconds upon exposure to water and sonic mixing energy. Such a timeframe is achieved in the Examples below and is necessary to convey long-lasting efficacy to a user.

Additionally, activation of the composition by a brush results in a shorter duration before reaching peak warming when compared to activation by hand. Although the duration of the warming may last a similar amount of time, the user senses the heat quicker and more intensely when brush activation is used.

Methods of Use

In another aspect, a method of cleansing is provided, comprising applying mixing energy to a mixture of water and a composition as disclosed herein.

In some embodiments, the cosmetic composition is used for cleansing, such as cleansing skin. The cosmetic composition is delivered to an area to be cleaned, such as a skin portion or a hair. Water can then be applied as well. In some embodiments, a sonic energy is applied to the mixture of water and the cosmetic composition. It is believed that sonic energy provides a more intense and longer lasting warming effect, when compared to manual application of the cosmetic composition. In other embodiments, manual energy (e.g., rubbing, scrubbing, massaging, washing, abrading, etc. the skin) is applied to the mixture of water and cosmetic composition.

In some embodiments, the mixture of water and the cosmetic composition is delivered to a skin portion. A sonic energy can be applied to the mixture of water and the cosmetic composition after delivery of the mixture to the skin portion or to hair, to cleanse the skin portion. In some embodiments, cleansing the skin portion includes exfoliating the skin portion. In certain embodiments, cleansing the skin portion includes removing make-up (when present) from the skin portion.

In one embodiment, the mixture of water and the composition is delivered to a skin portion.

In one embodiment, the mixing energy is applied to the mixture of water and the composition after delivery of the mixture to the skin portion, thereby cleansing the skin portion.

In one embodiment, cleansing the skin portion further includes exfoliating the skin portion.

In one embodiment, cleansing the skin portion further includes removing make-up from the skin portion.

The following examples are included for the purpose of illustrating, not limiting, the disclosed embodiments.

As used herein, all percentages are by weight (wt. %) of the total composition.

All numeric ranges are inclusive of narrower ranges; delineated upper and lower range limits are interchangeable to create further ranges not explicitly delineated. All ranges and values disclosed herein are inclusive and combinable. For examples, any value or point described herein that falls within a range described herein can serve as a minimum or maximum value to derive a sub-range, etc.

As used herein, the terms "comprising," "having," and "including" are used in their open, non-limiting sense.

The terms "a," "an," and "the" are understood to encompass the plural as well as the singular.

The expression "at least one" means "one or more" (and vice versa) and thus includes individual components as well as mixtures/combinations.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The foregoing description illustrates and describes the disclosure. Additionally, the disclosure shows and describes only the exemplary embodiments but, as mentioned above, it is to be understood that it is capable to use in various other combinations, modifications, and environments and is capable of changes or modifications within the scope of the disclosed concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

EXAMPLES

The following Examples are provided for illustrative purposes only, and are not intended to be limiting.

Example 1: Inventive Examples

In Table 1, three inventive compositions A, B and C were prepared and constitute the Group I. In Table 2, four inventive compositions D, E, F and G were prepared and constitute the Group II.

TABLE 1

Group I

| | | Formula | | |
|---|---|---|---|---|
| Phase | Ingredients/INCI US Name | A % | B % | C % |
| A1 | PROPYLENE GLYCOL | 42.6 | 40 | 40.4 |
| A2 | SODIUM LAUROYL GLUTAMATE | 10 | 8.8 | 8.5 |
| A3 | DIETHYLHEXYL SODIUM SULFOSUCCINATE | 15.6 | 0 | 2.1 |
| A4 | GLYCERIN | 31.7 | 51.3 | 49 |
| | WATER | 0.18 | 0 | 0.03 |

In making the formulations in the above tables, the following procedure was used. First, the propylene glycol and the glycerin were mixed together, then the diethyl sodium sulfosuccinate was dispersed (if present). Then, the sodium lauroyl glutamate was added into the mixture and homogenized for 5 minutes.

TABLE 2

Group II

| | Formula | | | | | | |
|---|---|---|---|---|---|---|---|
| Ingredient/ US INCI Name | D % | E % | F % | G % | H % | I % | J % |
| FRAGRANCE | 0.075 | 0.05 | 0.05 | 0.1 | 0.1 | 0 | 0.1 |
| KAOLIN | 0 | 15 | 10 | 0 | 15 | 0 | 0 |
| SODIUM LAUROYL GLUTAMATE | 8.5 | 8 | 8.5 | 8.5 | 8 | 10 | 8.5 |
| VITAMIN (TOCOPHERYL NICOTINATE) | 1 | 1 | 1 | 1 | 1 | 1 | 1 |
| THICKENER | 0 | 0 | 0 | 1 | 0 | 1 | 0 |
| SOLVENT | 38 | 36 | 38 | 38 | 36 | 32 | 38 |
| GLYCERIN | 23 | 11.5 | 13 | 21.9 | 11.4 | 14.6 | 21.9 |
| PROPYLENE GLYCOL | 27.3 | 26.3 | 27 | 27.3 | 26 | 23 | 27 |
| DIETHYLHEXYL SODIUM SULFOSUCCINATE | 2.1 | 2.1 | 2.1 | 2.1 | 2.5 | 18.3 | 2.5 |
| WATER | Q.S. | Q.S. | Q.S. | Q.S. | Q.S. | Q.S. | Q.S. |

In making the formulations in the above tables, the following procedure was used.

1. The propylene glycol, PEG-8, glycerin and polyacrylate crosspolymer-6 were hand mixed to wet polyacrylate crosspolymer-6.
2. Both side were swept and homogenized at a low speed for 5 min, then increase speed to medium speed for another 15 min. or till all polyacrylate crosspolymer-6 white specs disappeared.
3. With the homogenizer, temperature was rised to 60° C. or higher depending on the speed and how long it was mixed. For this batch, the total duration of homogenizer was 25 min.
4. The batch was swept and cooled to 50° C. before the sodium lauroyl glutamate was added.
5. Both side were swept and homogenized for about 10 min at low speed, to make sure all powder dispersed evenly without big chunks, then the cooling was continued.
6. Diethylhexyl sodium sulfosuccinate and tocopheryl nicotinate were added @ 40° C.
7. The fragrance was added @30 C.

Example 2: Evaluating the Thermal Effects of Foaming Warming Cleansers

In this Example, the three inventive compositions of the Group I according to the disclosed embodiments were evaluated. The results are shown in Table 3.

TABLE 3

| Formula | Total Significant Time Temperature was Above Average Control (Sec) | Peak Temperature (° F.) |
|---|---|---|
| A | 15.50 | 90.91 |
| B | 14.75 | 90.27 |
| C | 15.50 | 90.76 |

The purpose of the test was to assess the temperature change of three warming cleansers when used on the skin with an internal warming method.

Thermocouples were placed on subjects forearms and covered with a thin film (Tegaderm). Each cleanser was placed on different site of the forearms and activated with water (pre-warmed to 40° C./105° F.) manually or with a sonic brush. An esthetician cleansed the region over the thermocouple for a total of 15 seconds at each location.

Temperature readings were measured before and after the cleansing periods. Temperature measurements were captured at the rate of four times per second.

Results

The treatment sites recorded an increase in temperature as the warming cleanser was activated by manual or by sonic cleansing, forming a bell-shaped curve as the cleanser warmed then cooled (see FIG. 1). The peak/maximum temperature in the curve was identified for each subject. Data points representing 15 seconds before the peak temperature, the peak temperature, and 15 seconds following the peak temperature for each subject was analyzed.

The temperature measurements for each treatment were statistically compared to each other and to the control location temperatures. Average data points are illustrated in the FIG. 1.

For each formula, Table 3 above shows how long the temperature stayed above the average control and the peak temperature.

For each of the three formulas tested, all time points 15 seconds before and after the peak value for each subject was averaged. Formula A had the highest peak temperature between all three formulas at 90.9° F., which was 0.64° F. and 0.15° F. degrees higher than peak temperatures for Formula B (peak temperature; 90.3° F.) and Formula C (peak temperature; 90.8° F.), respectfully. An increase in temperature by 2-3 degrees was observed. It was observed that Formula C demonstrated a better spreadabillity compare to the Formula A and B.

There were no statistically significant differences for peak temperatures between Formula A vs. Formula B, Formula B vs. Formula C, or Formula A vs. formula C.

Example 3: Evaluation of Skin Surface Temperature Over Time

Twenty subjects completed the study and data from the thermocouple temperature sensors were recorded onto excel spreadsheets and the data was analyzed. The same protocol described in Example 2 was followed.

The temperature measurements for each cleanser and method of cleansing (Sonic and Manual Cleansing) were statistically compared to each other and to the control site temperatures. Average data points are illustrated in the FIGS. 3 and 4.

Below is a Table of the formula tested with their respective results.

TABLE 4

| Formula | Max Temp | | Duration Above Control (Seconds) | |
|---|---|---|---|---|
| | Manual | Sonic | Manual | Sonic |
| D | 90.41 | 92.22 | 12.25 | 18.25 |
| E | 90.32 | 92.18 | 14.50 | 18.25 |
| F | 90.11 | 92.38 | 12.75 | 17.75 |

All warming cleanser formulas had statistically higher peak temperatures with sonic cleansing compared to manual cleansing.

The duration of time that each cleanser was statistically above the temperature of the control site was longer with sonic cleansing than with manual cleansing.

Example 4: Comparative Examples

Evaluations of the warming and foaming effects have been conducted with different comparative examples. Using a scale from 0 to 5, with 0 showing no effects, with below 3 being unacceptable, above 3 being acceptable, and with 5 showing the best effects, compositions have been evaluated and the results are discussed below.

| | Formula | | | | | |
|---|---|---|---|---|---|---|
| Ingredients/INCI US Name | Comp. A % | Comp. B % | Comp. C % | Comp. D % | Comp. E % | Comp. F % |
| PROPYLENE GLYCOL | 30 | 40 | 35 | 30 | 35 | 30 |
| SODIUM LAUROYL GLUTAMATE | 10 | 0 | 0 | 30 | 15 | 10 |
| DIETHYLHEXYL SODIUM SULFOSUCCINATE | 10 | 30 | 0 | 20 | 25 | 15 |
| GLYCERIN | 50 | 30 | 65 | 20 | 25 | 45 |

Comparative Example A shows unacceptable warming and foaming effects. Regarding the warming effect, the evaluation number is below 3, meaning that the warming effect is unacceptable.

Comparative Example B shows unacceptable warming and foaming effects with a number below 3. In this composition, the percentage of one of the foaming agent is higher than the range defined for the inventive example. The diethylhexyl sodium sulfosuccinate is equal to 30% which is higher than the highest range of the foaming surfactant.

Comparative Example C shows unacceptable warming and foaming effects with a number below 3. Both foaming surfactants are absent.

Comparative Example D shows unacceptable warming with a number below 3. Regarding the foaming effect, the evaluation number is below 3, meaning that the foaming effect is unacceptable as well.

Comparative Example E shows unacceptable warming with a number below 3. Regarding the foaming effect, the evaluation number is also below 3, meaning that the foaming effect is unacceptable. The ingredients are out of the range of the inventive examples.

Comparative Example F shows unacceptable warming with a number below 3. Regarding the foaming effect, the evaluation number is also below 3, meaning that the foaming effect is unacceptable. The ingredients are out of the range of the inventive examples.

Example 5: The Base

Three of the main components were screened and evaluated: surfactants, thickeners and warming agents. Once the best ingredients were selected, other elements such as clay, fragrance, and polymers for stability were screened, selected and added.

a) Surfactants Screening

Surfactants were tested according to the foam criteria. The main property required to select the surfactants was the fact that it needed to be compatible with the anhydrous system. To screen out the surfactants, simple formulas were made by combining the surfactant and the solvents and a quick lab evaluation on subjects hands using a 5 pt scale for foam was done.

Below is a Table of the different surfactants tested with their respective results.

TABLE 5

Surfactants

| SURFACTANTS | FOAM |
|---|---|
| SODIUM LAURYL SULFATE | + |
| POTASSIUM LAURATE | + |
| SODIUM LAUROYL GLUTAMATE | ++ |
| LAURETH-5 CARBOXYLIC ACID | + |
| LAURETH-4 | + |
| DIETHYLHEXYL SODIUM SULFOSUCCINATE | ++ |

Table 5 shows that the sodium lauroyl glutamate and diethylhexyl sodium sulfosuccinate provided the best foaming properties, as shown by the positive (++) results.

b) Thickeners Screening

Thickeners were also added to the formula as some stability issues were observed. Thickeners were tested according to their stability with the surfactants which started to separate from the solvents. Below is a Table of the different thickeners tested with their results.

TABLE 6

Thickeners

| INCI Name | Classification | Stability |
|---|---|---|
| Acrylates/C10-30 Alkyl Acrylate Crosspolymer [1] | Acrylate | + |
| Polyacrylate Crosspolymer-6 [2] | Acrylate | +++ |
| Disteardimonium Hectorite [3] | Clay | + |
| MICA (And) SILICA [4] | Silica | + |
| Hydroxypropyl Guar [5] | Holoside | + |
| Pullulan [6] | Holoside | + |
| Xanthan Gum [7] | Holoside | + |
| Xanthan Gum [8] | Holoside | + |
| Peg-20 Methyl Glucose Sesquistearate [9] | Sugar Ester | +++ |
| Dimethicone/Vinyl Dimethicone Crosspolymer [10] | PDMS | + |

[1] Carbopol ultrez 20;
[2] Sepimax Zen;
[3] Bentone 38 VCG;
[4] Velvetveil A;
[5] Jaguar HP 105;
[6] Pullulan;
[7] Keltrol CG-T;
[8] Rhodicare CFT;
[9] Glucamate SSE Emulsifier;
[10] Dow Corning 9506 Powder.

The main property required to select the thickener was the fact that it needed to be compatible with the anhydrous system. Polyacrylate Crosspolymer-6 and Peg-20 Methyl Glucose Sesquistearate provided the best stability properties, as shown by the positive (+++) results.

c) Warming Enhancers

Different warming enhancers were tested and can be added to the composition in order to improve the warming effect. Below is a Table showing different warming enhancers that can be added to the composition.

| INCI Name | Warmth | Appearance | Comfort |
|---|---|---|---|
| Tocopheryl Nicotinate | ++ | ++ | ++ |
| Vanillyl Butyl Ether | ++ | ++ | + |
| Ginger Extract | ++ | + | ++ |

The warming enhancement was tested by evaluating three criteria the warmth, the appearance and the comfort. The tocopheryl nicotinate exhibits the best results for the three criteria with (++) results.

What is claimed is:

1. An anhydrous warming foaming cleanser composition comprising:
   a) one or more foaming surfactants selected from the group consisting of sodium lauroyl glutamate and diethylhexyl sodium sulfosuccinate,
   wherein the total amount of foaming surfactant is at least about 8% by weight of the total weight of the composition;
   b) a first and a second polyol;
   c) from about 28% to about 50% by weight of a third polyol selected from the group consisting of PEG-4, PEG-6, PEG-8, and the mixtures thereof;
   d) a thickener agent selected from the group consisting of polyacrylate crosspolymer-1, polyacrylate crosspolymer-6, polyacrylate crosspolymer-9, polyacrylate crosspolymer-11, and the mixtures thereof.

2. The composition of claim 1, wherein the composition produces a warming effect when mixed with water during a cleansing process.

3. The composition of claim 1, wherein the one or more foaming surfactants are present in an amount from about 8% to about 15% by weight of the total weight of the composition.

4. The composition of claim 1, wherein the one or more foaming surfactants are present in an amount from about 8% to about 10% by weight of the total weight of the composition.

5. The composition of claim 1, wherein the first polyol is propylene glycol.

6. The composition of claim 1, wherein the second polyol is glycerin.

7. The composition of claim 1, wherein the first polyol is present in an amount from about 20% to about 40% by weight of the total weight of the composition.

8. The composition of claim 7, wherein the first polyol is present in an amount from about 23% to about 33% by weight of the total weight of the composition.

9. The composition of claim 8, wherein the first polyol is present in an amount from about 25% to about 28% by weight of the total weight of the composition.

10. The composition of claim 1, wherein the second polyol is present in an amount from about 10% to about 60% by weight of the total weight of the composition.

11. The composition of claim 10, wherein the second polyol is present in an amount from about 15% to about 50% by weight of the total weight of the composition.

12. The composition of claim 11, wherein the second polyol is present in an amount from about 18% to about 40% by weight of the total weight of the composition.

13. The composition of claim 1, wherein the third polyol comprises PEG-8.

14. The composition of claim 13, wherein PEG-8 is present in an amount from about 25% to about 50% by weight of the total weight of the composition.

15. The composition of claim 14, wherein PEG-8 is present in an amount from about 30% to about 45% by weight of the total weight of the composition.

16. The composition of claim 15, wherein PEG-8 is present in an amount from about 35% to about 40% by weight of the total weight of the composition.

17. The composition of claim 1, wherein the thickener agent comprises polyacrylate crosspolymer-6.

18. The composition of claim 1, wherein the thickener agent is present in an amount from about 0.1% to about 2% by weight of the total weight of the composition.

19. The composition of claim 18, wherein the thickener agent is present in an amount from about 0.5% to about 1.5% by weight of the total weight of the composition.

20. The composition of claim 19, wherein the thickener agent is present in an amount from about 0.7% to about 1.2% by weight of the total weight of the composition.

21. The composition of claim 1, further comprising:
   e) a warming enhancer selected from the group consisting of tocopheryl nicotinate, vanillyl butyl ether, ginger, *capsicum* extract, volcanic ash.

22. The composition of claim 21, wherein the warming enhancer comprises tocopheryl nicotinate.

23. An anhydrous warming foaming cleanser composition comprising:
   a) sodium lauroyl glutamate and diethyl sodium sulfosuccinate;
   b) propylene glycol and glycerin;
   c) a polyacrylate crosspolymer-6;
   d) PEG-8; and
   e) tocopherol nicotinate.

24. A method of cleansing skin, comprising:
   applying to skin a mixture of water and the composition of claim 1; and
   applying a manual or sonic energy to the mixture to cleanse the skin.

* * * * *